(12) United States Patent
Tsai et al.

(10) Patent No.: US 8,323,254 B2
(45) Date of Patent: Dec. 4, 2012

(54) SILICONE BASED TUBE FOR TRANSPORTING MALODORIFOROUS MATTER FROM THE HUMAN BODY

(75) Inventors: Mingliang Lawrence Tsai, Holmdel, NJ (US); Christopher Gregory, Newtown, PA (US)

(73) Assignee: ConvaTec Technologies, Inc., Las Vegas, NV (US)

( * ) Notice: Subject to any disclaimer, the term of this patent is extended or adjusted under 35 U.S.C. 154(b) by 0 days.

(21) Appl. No.: 11/877,691

(22) Filed: Oct. 24, 2007

(65) Prior Publication Data
US 2008/0103463 A1    May 1, 2008

Related U.S. Application Data

(60) Provisional application No. 60/863,053, filed on Oct. 26, 2006.

(51) Int. Cl.
*A61M 1/00* (2006.01)
(52) U.S. Cl. ...................... 604/317; 604/93.01
(58) Field of Classification Search ............ 604/317, 604/327, 332–345, 96.01–103.14, 19, 48, 604/93.01, 525, 27, 28, 104, 275–277
See application file for complete search history.

(56) References Cited

U.S. PATENT DOCUMENTS

| | | | |
|---|---|---|---|
| 4,381,765 A | 5/1983 | Burton | |
| 4,662,890 A | 5/1987 | Burton | |
| 4,721,508 A | 1/1988 | Burton | |
| 4,778,553 A | 10/1988 | Wood | |
| 5,093,194 A * | 3/1992 | Touhsaent et al. | 428/349 |
| 5,290,613 A | 3/1994 | Shuetz | |
| 5,522,801 A * | 6/1996 | Wang | 604/103.05 |
| 5,569,216 A | 10/1996 | Kim | |
| 5,654,054 A * | 8/1997 | Tropsha et al. | 428/36.6 |
| 6,050,928 A | 4/2000 | Tsai | |
| 2004/0039348 A1 | 2/2004 | Kim | |
| 2005/0054996 A1 | 3/2005 | Gregory | |
| 2005/0137526 A1 | 6/2005 | Machado | |
| 2006/0100595 A1 | 5/2006 | von Dyck | |
| 2006/0189951 A1 | 8/2006 | Kim | |

FOREIGN PATENT DOCUMENTS
EP   0469926   2/1992
* cited by examiner

*Primary Examiner* — Tatyana Zalukaeva
*Assistant Examiner* — Benedict L Hanrahan
(74) *Attorney, Agent, or Firm* — Stuart E. Krieger

(57) ABSTRACT

A tube assembly for carrying malodoriforous matter from the human body comprises a silicone based tube having a central bore for the malodoriforous matter, and a tubular sleeve member comprising an odor barrier material, the silicone based tube and the tubular sleeve member being arranged one within the other such that the tubular sleeve member provides an odor barrier to obstruct leakage of odors from malodoriforous matter in the bore of the silicone based tube. The tube assembly is especially suitable for use in fecal or bowel management apparatus.

9 Claims, 7 Drawing Sheets

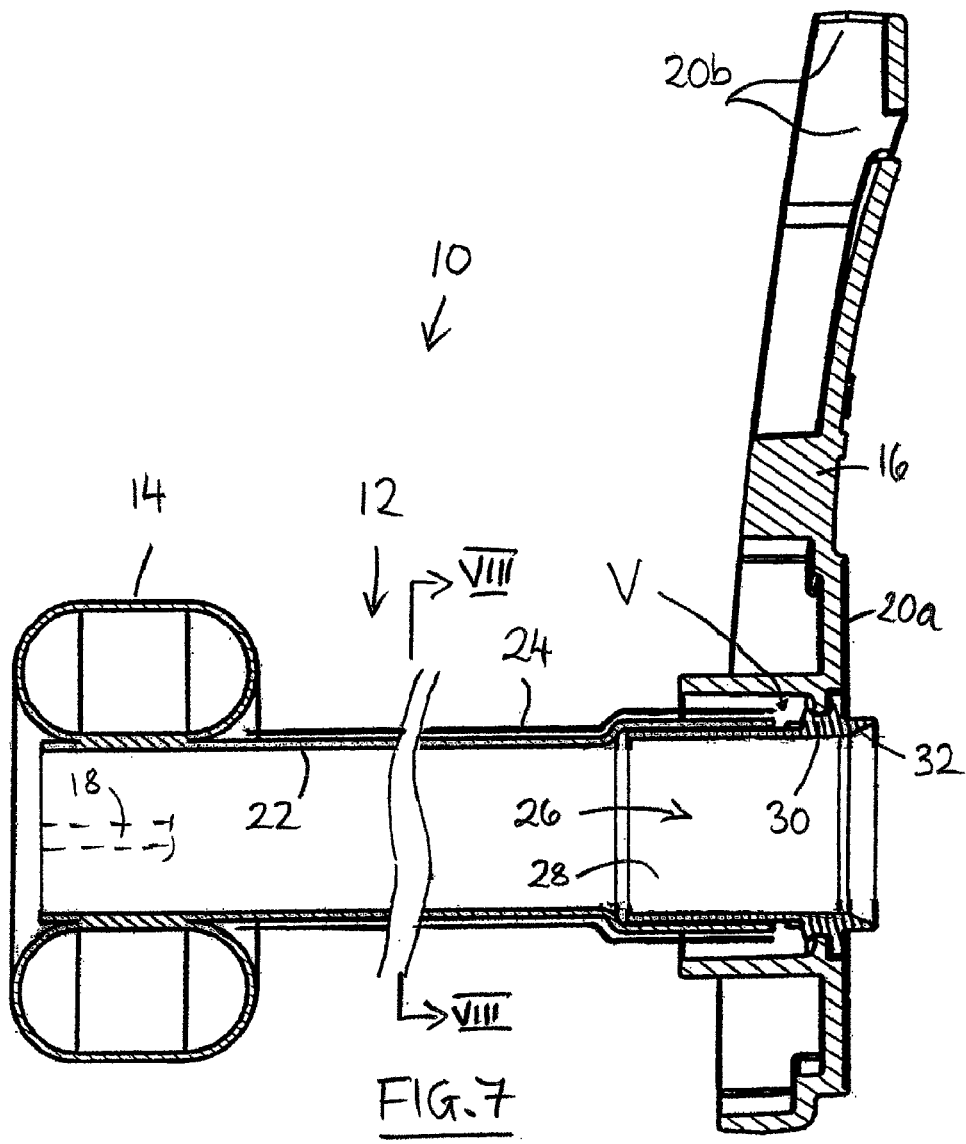
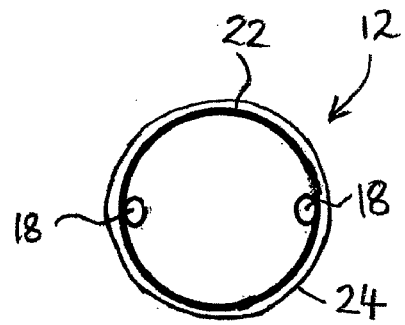

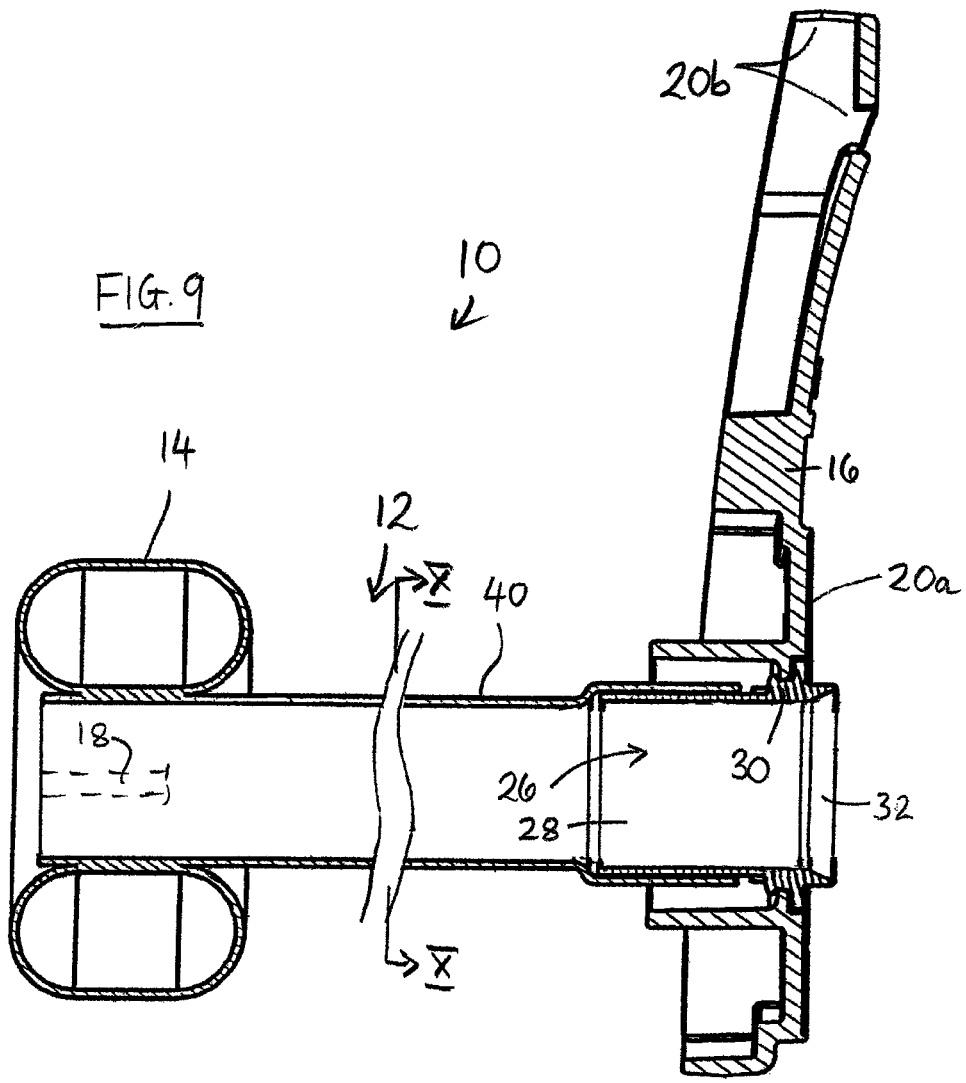
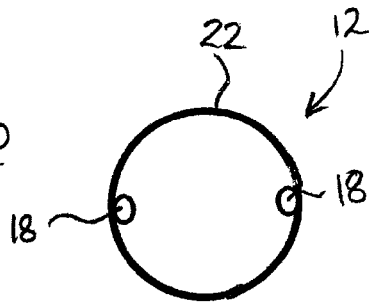

SILICONE BASED TUBE FOR TRANSPORTING MALODORIFEROUS MATTER FROM THE HUMAN BODY

FIELD OF THE INVENTION

The present invention relates to a silicone based tube for transporting malodoriferous matter from the human body. The tube may, for example, be used in bowel management apparatus for hygienically collecting fecal matter from the human body, but the invention may find use in any system for transporting malodoriferous matter from the human body.

BACKGROUND TO THE INVENTION

US 2005/0054996 and US 2005/0137526 describe bowel management apparatus including a silicone tube having at its distal end a balloon cuff that may be inflated to locate the distal end of the tube inside a wearer's rectum. The proximal end of the tube is fitted with a connector for making a connection to a fecal collector chamber. It is difficult to find an ideal single material that exhibits all of the desired characteristics for making the tube. Silicone is used for its biocompatibility, flexibility and comfortable wear characteristics. However, silicone is known to have a relatively high gas transpiration (or transmission) rate, which might lead to malodors leaking through the material forming the tube, especially if the tube has a relatively long run to the fecal collection chamber. The human nose is especially sensitive to flatus, and foul odors are embarrassing and unpleasant for the wearer and caregivers.

In US 2005/0054996, a parylene coating is applied to the surfaces of the silicone material to improve its odor barrier properties. However, in some cases, the parylene coating might not be ideal because:
(i) the parylene coating tends can be highly crystalline, and so might be vulnerable to micro-cracking when the silicone tube is flexed or twisted or stretched in use, leading possibly to a reduction in the integrity of the odor barrier;
(ii) the parylene coating tends to be relatively thin. Any irregularities in the deposited thin coating could further risk the integrity of the odor barrier. For example, the odor barrier of parylene at 25 thickness is reported to be 30 $cc/m^2/day$ at 23° C. However, a thin coating in the range of 1-2 μm thickness could result in an oxygen transmission rate much higher, in the 380-760 $cc/m^2/day$ range, which might be too high to provide sufficient odor barrier. Any micro-cracking in parylene would even worsen already compromised thin layer of barrier coating;
(iii) the coating process involves polymerizing and vacuum depositing the parylene onto the silicone tube, which is a difficult and expensive manufacturing process, thus increasing the manufacturing costs; and
(iv) there is a requirement to mask some key parts of the device against coating by parylene, which further complicates the manufacturing process;

For reference, other bowel and stoma appliances employing silicone based tubes include U.S. Pat. Nos. 4,381,765, 4,662,890, 4,721,508 and 5,569,216, and published U.S. Patent Applications 2004/0039348, 2006/0100595 and 2006/0189951. However, none of these publications address the issue of odor leakage through the silicone material.

The present invention has been directed to enhancing the characteristics of the silicone tube for handling malodoriferous matter. In particular, it would be desirable to provide an alternative odor barrier technique for the silicone tube, which can achieve at least approximately the same degree of odor barrier as a parylene coating, but which may be less disadvantageous.

SUMMARY OF THE INVENTION

Broadly speaking, one aspect of the invention is to provide a silicone tube with an inner and/or outer tubular sleeve member, the tubular sleeve member comprising an odor barrier material.

The term odor barrier material is intended to include any material that has a greater resistance to transmission or permeation of odors, than silicone, preferably at least an order of magnitude greater. The invention can significantly enhance the odor barrier properties of the silicone tube by at least slowing down, or preferably substantially stopping, permeation of unpleasant odors from the silicone tube. Moreover, the provision of a distinct sleeve member inside or outside the silicone tube can avoid the problems associated with chemically depositing a thin film coating on the silicone. In particular, it can avoid the need for complex and expensive deposition processes, and it can avoid the issues of the thickness and integrity of the deposited film.

Preferably, the sleeve member is flexible, in order not to hinder bending of the silicone tube. Preferably the sleeve member is as flexible as the silicone tube and ideally more flexible than the silicone tube.

Preferably the wall thickness of the sleeve member is less than that of the silicone tube, in order not to increase substantially the size of the tubing and/or not to decrease the bore size of the internal passage inside the silicone tube. Preferably, the wall thickness of the sleeve member is not more than about 1/10 of that of the silicone tube.

In one form, the sleeve member is made of flexible film material. A suitable material is, for example, the flexible film conventionally used for the production of ostomy pouches and urine pouches. The film may be a laminate including the odor barrier material layer and one or more non-odor barrier materials. It is also possible to have a homogenous film, such as nylon, to bond well to silicone by adhesive and to block odor transmission. The film may be extruded in a sleeve shape, or the sleeve may be formed from sheet form by wrapping the sheet into a closed loop sleeve shape and sealing the edges together to form a longitudinal seam. If desired, the sheet may be rolled to form a sleeve of several layers before sealing.

In one form, the sleeve member is fitted outside the silicone tube. The sleeve is secured in place by any suitable means. Placing the sleeve outside the tube avoids the need to support the sleeve internally, since the shape of the sleeve is determined by the silicone tube. An especially preferred technique is to provide a sleeve made of material that shrinks when subjected to heat, and to heat the sleeve in order to shrink the sleeve around the silicone tube. This can provide firm anchoring of the sleeve around the silicone tube, without having to use any additional fastening device or adhesive. Alternatively, the sleeve may made slightly larger than the silicone tube, and the sleeve may be fed over the silicone tube, and fastened in position either by adhesive or by a mechanical fastening. Alternatively, the sleeve may be formed from sheet material wrapped around the silicone tube.

In another form, the tubular sleeve member comprises an inner liner fitted inside the silicone tube. The inner liner is preferably secured in place by adhesive and/or by a mechanical device, to ensure that the liner is not displaced axially in use. Axial displacement could dislodge the liner, removing the odor barrier protection from a local area. The inner liner may be secured only at its ends if desired.

A vent path may be provided for gas in the space between the silicone tube and the tubular sleeve member. The vent path may avoid gas collecting between the two tubes, which otherwise might cause undesirable ballooning of the collection bag or constricting of the waste path. Gas could enter the space between the tubes during manufacture, or during transportation, or during use of the tube. Preferably, the vent path vents into a region communicating with a flatus filter or it may vent into the collection volume for the fecal matter. If the sleeve member is on the inside of the silicone tube and creates a seal with the collection volume, the venting can be directly to atmosphere.

A further independent, yet closely related, aspect of the invention is to provide a tube made of a laminate comprising a layer of silicone based material, and a layer of odor barrier material. These layers are laminated together either prior to, or at the same time as, the formation of the silicone based material into a tubular form.

A further independent, yet closely related, aspect of the invention is to produce a tube including a layer of silicone based material and a layer of odor barrier material by at least one of the following processes: extrusion, coextrusion, extrusion coating, or adhesive lamination.

These aspect of the invention results in a single tube member incorporating both the silicone based material and the odor barrier material laminated together. This aspect also avoids the problems in the prior art associated with chemically depositing a thin film coating on the silicone. In particular, it can avoid the need for complex and expensive deposition processes, and it can avoid the issues of the thickness and integrity of the deposited film.

A further independent aspect of the invention provides a silicone based tube provided with a layer of odor barrier material for obstructing leakage of odors from material carried inside the tube. Preferably, the barrier material comprises at least one selected from: poly(vinylidene chloride) (PVDC); poly(vinyl alcohol) (PVOH); an ethylene vinyl alcohol copolymer (EVOH); a polyamide (nylon) or co-polyamide or polyamide blends selected from PA-6, PA-6, 6, PA-11, and PA-12, amorphous polyamides, MXD6 polyamide; a polyester (PET); a polyester elastomer; glycol-modified polyester (PETG); a polyester or co-polyester blend; poly(acrylonitrile) (PAN); polyurethane (PUR); polyvinyl chloride (PVC); polychlorotrifluoro ethylene (PCTFE); styrene-acrylonitrile copolymers; acrylonitrile-butadiene-styrene terpolymers; poly(methyl methacrylate); styrene-butadiene copolymers.

Other features and advantages of the present invention will be apparent from the following description of preferred embodiments. While features believed to be of importance are described above and in the appended claims, the Applicant may seek protection for any inventive feature described herein and/or illustrated in the drawings whether or not emphasis has been placed thereon.

BRIEF DESCRIPTION OF THE DRAWINGS

FIG. 7 is a cross-sectional view showing a second embodiment.

FIG. 8 is a view along the line VIII-VIII of FIG. 7.

FIG. 9 is a cross-sectional view through a wall portion of the tube in a third embodiment.

FIG. 10 is view along the line X-X of FIG. 9.

DETAILED DESCRIPTION OF THE INVENTION

Figure 1:
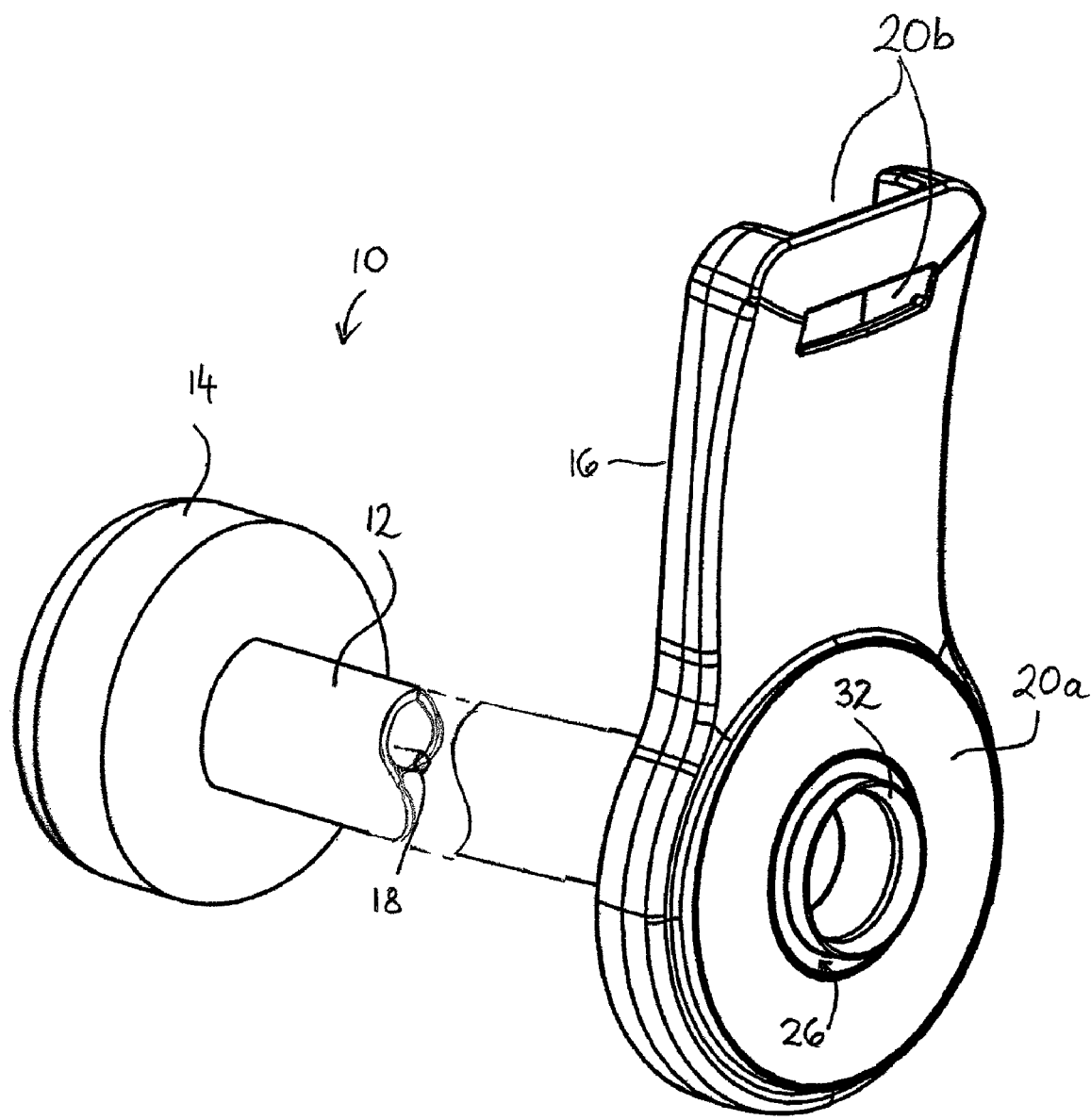
FIG. 1 is a perspective view of a first embodiment of a bowel management apparatus in accordance with the present invention.

Referring to FIG. 1, a bowel management apparatus 10 generally comprises a tube 12 at the distal end of which is provided an annular balloon cuff 14, and at the proximal end is provided a support connector 16. The distal end is for insertion into the rectum of a wearer, for example a bedbound person. The balloon cuff 14 is inflatable via an inflation conduit 18 for retaining the distal end in the rectum. The tube 12 functions to hygienically transport excreted stool and flatus from the body to a fecal collection container (not shown), such as a fecal bag. The support connector 16 provides a connection point to the fecal collection container and an attachment point for attaching to the person's bed. In the current embodiment, the support connector 16 comprises an annular landing zone 20a for adhesive attachment to the fecal collection container or an injection molded flange for mechanically coupling to the fecal collection container, and an aperture 20b for receiving an attaching strap (not shown).

The tube 12 may be of any desired length, for example from about a few centimeters (e.g., the minimum distance for the tube to exit the rectum to at least the exterior skin surface), up to the order of 1-2 meters or more (e.g., to provide a tube length sufficient to reach the edge of a bed while still allowing the wearer to move around in the bed). In the illustrated form, the tube 12 consists of a single length of material, but the invention envisages that the tube 12 could be made of plural tube segments.

Figure 2:
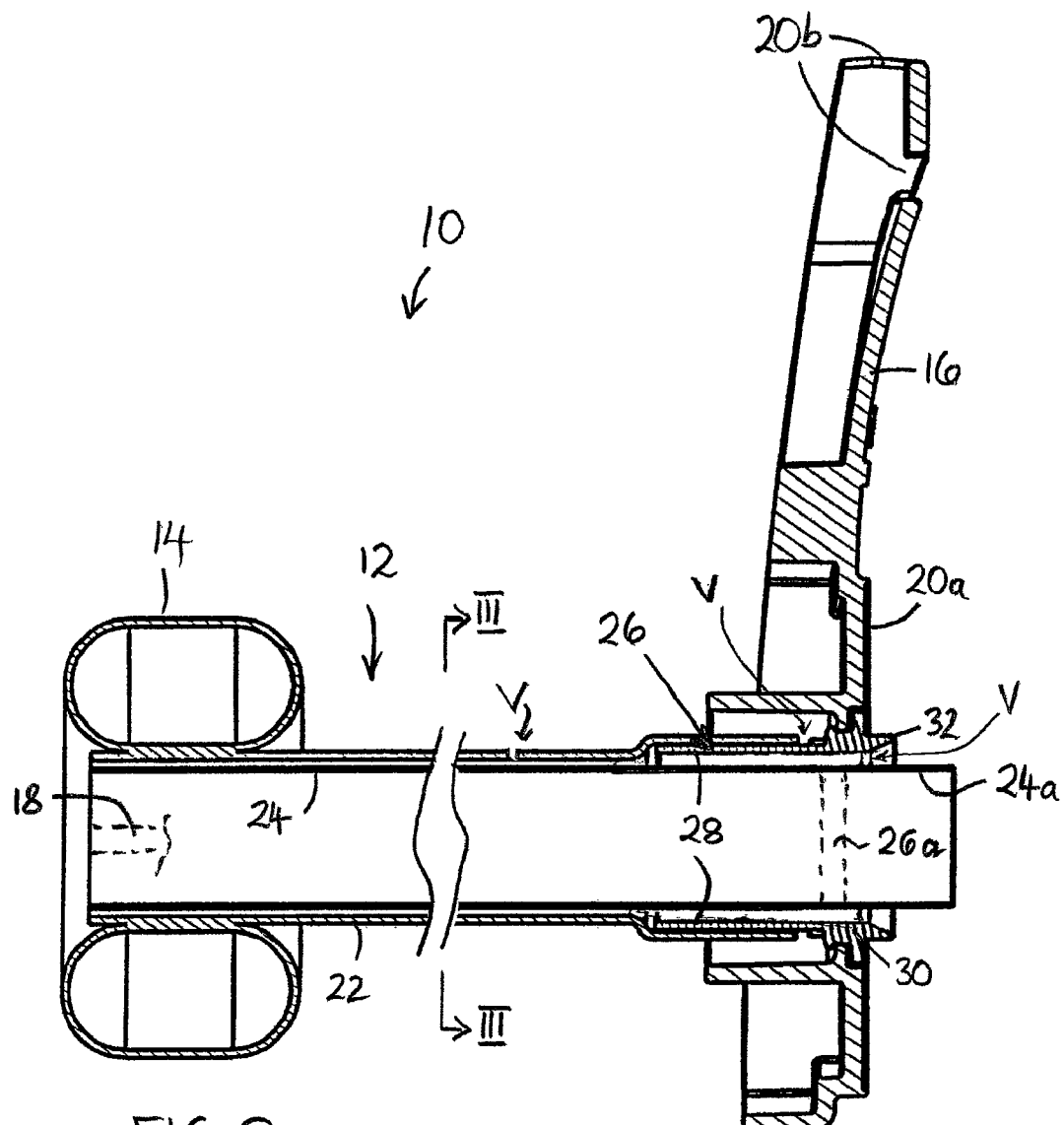
FIG. 2 is a cross-sectional view of the first embodiment.

Referring to FIG. 2, the tube 12 generally comprises a first tube member 22 and a second tube member 24 placed one within the other. The first tube member 22 is a primary shape defining tube made of a silicone material, for example, silicone rubber. Silicone is chosen for its biocompatibility, flexibility and comfort characteristics. The first tube member 22 is soft enough to enable the tube to be flexible and conformable, while being sufficiently stiff to retain an open tubular shape when not compressed. In the present embodiment, the first tube member 22 has a generally round cross-section shape, with an outer diameter of about 2-4 cm, and a wall thickness of between about 0.25 and 5 mm. The second tube member 24 is an odor barrier sleeve comprising an odor barrier material. The odor barrier material has a greater resistance to transmission or permeation of odors, than silicone, preferably at least an order of magnitude greater. The second tube member 24 is generally as flexible as the first tube member 22 so as not to obstruct the flexibility of the tube 12.

The second tube member 24 has a thinner wall thickness than the first tube 22, for example, not more than about 1/10 of the wall thickness of the first tube 22. Generally, in such a thin and flexible film, the second tube member 24 might not retain an open tubular shape itself, but instead, the second tube member 24 is supported by the first tube member 22 to the extent necessary.

The provision of the second tube member 24 can greatly enhance the odor barrier properties of the tube 12 compared to just the silicone tube member 22 alone. Although the characteristics of silicone material of the first tube member 22 are excellent in many respects, one area where silicone lacks performance is its odor barrier characteristics. Odor leakage may be especially noticeable in longer tube lengths but may also be evident in shorter lengths. The invention can significantly enhance the odor barrier properties of both long (e.g., more than about 50 cm, or more than 100 cm), and short silicone tubes by at least slowing down, or preferably substantially stopping, permeation of unpleasant odors from the silicone tube. Moreover, the provision of the odor barrier as a distinct sleeve member can avoid the problems associated with chemically depositing a thin film coating on the silicone. In particular, it can avoid micro-cracking of the coating and the need for complex and expensive deposition processes, and it can avoid the issues of the thickness and integrity of the deposited film. Generally, the second tube member 24 will retain its full integrity throughout the use life of the silicone first tube member 22, even with repeated flexing, stretching and twisting of the tube 12 in its normal everyday use.

Any suitable material with odor barrier properties may be used for the second tube 24. One preferred example is plastics film conventionally used for manufacturing ostomy pouches. Such plastics film is relatively inexpensive, strong, has good workability (e.g., with adhesives or welding), known biocompatibility and excellent odor barrier properties. An example plastics film comprises an odor barrier of poly(vinylidene chloride) (PVDC). Such a barrier polymer can be coextruded or laminated with one of more layers of ethylene vinyl acetate (EVA). Another preferred example is nylon film, which provides good odor barrier properties and provides a good adhesive bond to silicone. Other examples of odor barrier materials include poly(vinyl alcohol) (PVOH), ethylene vinyl alcohol copolymers (EVOH), a polyamide or co-polyamide or polyamide blends selected from PA-6, PA-6,6, PA-11, and PA-12, amorphous polyamides, MXD6 polyamide, polyesters (PET), polyester elastomers, glycol-modified polyester (PETG), a polyester or co-polyester blend, poly(acrylonitrile) (PAN), polyurethane (PUR), polyvinyl chloride (PVC), fluoropolymers such as polychlorotrifluoro ethylene (PCTFE), styrene-acrylonitrile copolymers, acrylonitrile-butadiene-styrene terpolymers, poly(methyl methacrylate), styrene-butadiene copolymers, polyacrylonitrile, and homopolymers, copolymers, or blends of above polymers.

The plastics film may be extruded in the tubular sleeve shape, or a sheet of the film material may be rolled around a former and secured in its rolled up form, for example, by adhesive or by a welded seam. The sleeve may comprise a single layer of film, a multilayer film, cross wound tube, or the film may be rolled on itself several times.

The following description describes two alternative embodiments, a first in which the second tube member (odor barrier sleeve) 24 is fitted inside the first tube member 22; and a second embodiment in which the second tube member (odor barrier sleeve) 24 is fitted outside the second tube member 22. The following table illustrates the comparative performance of both embodiments compared to a silicone tube without any odor barrier, and a silicone tube with a parylene coating, by using the so-called "Onion Test" (British Standard 7127: Part 101: 1991) in which the odor barrier properties are assessed according to whether odor from an onion when contained by the test material in a closed system can be detected by the human nose. Films were also tested for their odor barrier using oxygen transmission rate (OTR), ASTM D3985:

| Emb. | TUBE TYPE | Oxygen Transmission Rate (OTR), cc/m$^2$/day at 23° C., 90% RH | ONION TEST |
|---|---|---|---|
|   | Silicone tube without odor barrier | 40,000 | Very Strong smell |
|   | Silicone tube with parylene coating | >6,000 | Strong smell |
| 1 | Silicone tube with inner odor barrier sleeve of PVdC-containing film | 50 | No smell detected |
| 1 | Silicone tube with inner odor barrier sleeve of nylon film | 100 | No smell detected |
| 2 | Silicone tube with outer odor barrier sleeve made of shrinkable EVOH-containing barrier film | 50 | No smell detected |

Oxygen transmission rate (OTR) is used as a reasonable predictor of the device's low permeability to the smaller odorous molecules in human fecal matter, while onion test is used as an overall predictor of the device's resistance to the permeation of malodoriferous compounds generated from the digestive system in the human body.

As noted in the table, silicone tubing without odor barrier had an extremely high OTR of around 40,000 cc/m$^2$/day, and did not provide any resistance against onion odor. Although the parylene coating of silicone tube used in the prior art had better OTR than that of silicone tube without odor barrier material, the level of OTR was still considered high at around 6,000 cc/m$^2$/day and did not provide sufficient barrier against onion odor. In all three examples according to the invention, the use of tubular sleeve materials significantly reduced OTR to a range less than 1,000 cc/m$^2$/day and preferably less than 500 cc/m$^2$/day. As shown in the table, all three examples offered great resistance against onion odor.

Although not tested, the invention also encompasses the possibility of providing odor barrier sleeve members both inside and outside the silicone tube. However, it is currently believed that such a combination is not essential, since the above tests illustrate that a single odor barrier sleeve member, either inside or outside the silicone tube provides excellent odor barrier performance. The choice depends on the desired production techniques and the desired properties of the tube 12 depending on a specific application in use.

Figure 3:
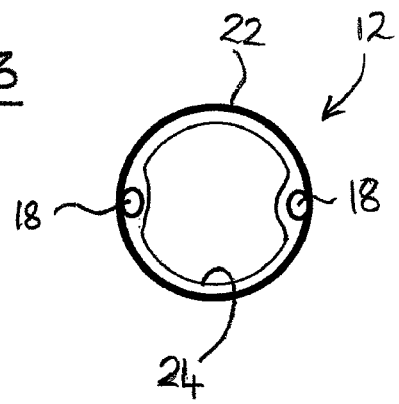
FIG. 3 is cross-sectional view along the line III-III of FIG. 2.

In the first embodiment illustrated in FIGS. 2 and 3, the second tube (sleeve) member 24 is provided as an internal liner inside the first tube member 22. The second tube member 24 is fastened to the first tube member 22, for example, completely around its circumference at the distal end (i.e., patient end) and substantially along its entire length, or at least at longitudinally and/or circumferentially spaced apart positions, or at least one longitudinal position. The attachment may be by means of adhesive. The attachment serves to create a seal between the first and second tubes at the patient end and locate the second tube member 24 axially, in order to prevent the second tube member 24 from being dislodged or displaced axially, for example by passage of fecal matter within the tube 12, or if the tube 12 is milked by a caregiver to peristaltically advance fecal matter along the tube 12. The fastening may optionally support the second tube member 24 and thus keeps the tubular space generally open and unobstructed by preventing the second tube member from collapsing inside the first tube member 22. However, in the preferred embodiment, the second tube member 24 is fastened only at or near one or both ends thereof.

In the case where the second tube member 24 is not fastened to the first tube member 22 along its entire length, a vent path "V" is provided for allowing any gas trapped between the first and second tuber members 22 and 24 to escape. Gas may enter the space between the first and second tube members 22 and 24 either during manufacture, or it may permeate through the silicone wall of the first tube member 22. Generally, it is desired to allow such gas to vent away easily, so as to avoid constricting the internal bore inside the first and second tube members 22 and 24. The vent path may, for example, comprise a small aperture in the wall of the first tube member and/or a vent aperture at the proximal end of the tube 12.

An example material for the second tube member 24 is a 75 μm thick PVdC-containing film from Cryovac. Another preferred example is nylon film. The second tube member 24 may have a diameter slightly smaller than the first tube member 22, for example about 1.9 cm, or slightly bigger than the first tube member 22, for example about 2.13 cm. The film may be attached in position by any suitable adhesive, for example, a two-part silicone adhesive by Nusil Technology, a RTV silicone adhesive made by CRC Industries, Inc.

The tube 12 may be made by forming the first and second tube members 22 and 24 separately, then inserting the second tube member 24 inside the first, and advancing one tube member relative to the other, to draw the second tube member 24 to extend completely through the first tube member 22.

Within the first tube member 22, the second tube member 24 sits radially inwardly of any secondary conduits 18 carried by the first tube member 22, such as the inflation conduit 18 mentioned above, and/or an irrigation conduit for irrigating the rectum. Such an arrangement can allow an external fluid connection to be made through the wall of the first tube member 22 to the secondary conduit 18, without breaching the second tube member 24, and thus without breaching the integrity of the odor barrier. This arrangement is especially suitable when the secondary conduit 18 is integrally formed with, or is attached to, the wall of the first tube member 22. Alternatively, in a modified form not shown, if the secondary conduit 18 is a separate conduit not integrally attached to the first tube member 22, then the secondary conduit 18 could run inside the bore of the second tube member 24 if desired.

As can be seen in FIG. 2, the tube 12 is coupled to the support coupling 16 by a flanged adapter tube 26. The adapter tube 26 generally comprises a tubular spigot 28 with locating flanges 30 and a mouth section 32. In use, the tubular spigot 28 is inserted into the proximal end of the first tube member 22 to affix to the proximal end of the first tube member 22 either by adhesive or by a tight friction fit. The adapter tube 26 is secured to the support coupling 16 by means of the locating flanges 30 which interlock against the support coupling 16.

In the first embodiment, the second tube (sleeve) member 24 is configured to extend longitudinally beyond the proximal end of the first tube member 22, and to pass inside the adapter tube 26 to define a protruding portion 24a that protrudes slightly from the mouth section 32 and the support coupling 16. The portion of the second tube (sleeve) member 24 inside the adapter tube 26 is optionally secured to the adapter tube 26, for example, by adhesive, welding or the introduction of an inner ring (shown in phantom at 26a) to trap the film against the inside of the adapter tube. In use, the protruding portion 24a fits just inside the aperture of a fecal collection container that is secured to the support coupling 16, to thereby provide a continuous odor barrier from the tube 12, through the adapter tube 26 and support coupling 16 into the fecal collection chamber.

Figure 4:
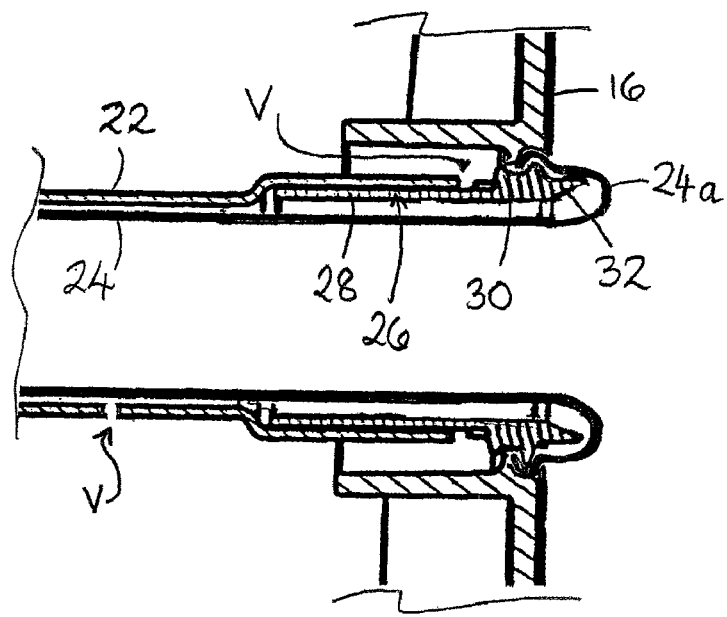
FIG. 4 is a cross-sectional view showing a modification of the first embodiment, with a different proximal end arrangement.

In a modified form of the first embodiment illustrated in FIG. 4, the protruding portion 24a of the second tube member 24 is folded back around the locating flanges 30 of the adapter tube 26, so as to be trapped between the locating flanges 30 and the support connector 16 when the adapter tube 26 is fitted to the support connector 16. With this configuration, no adhesive is necessary at the proximal end of the tube 12 to fasten the proximal end of the second tube member 24.

Figure 5:
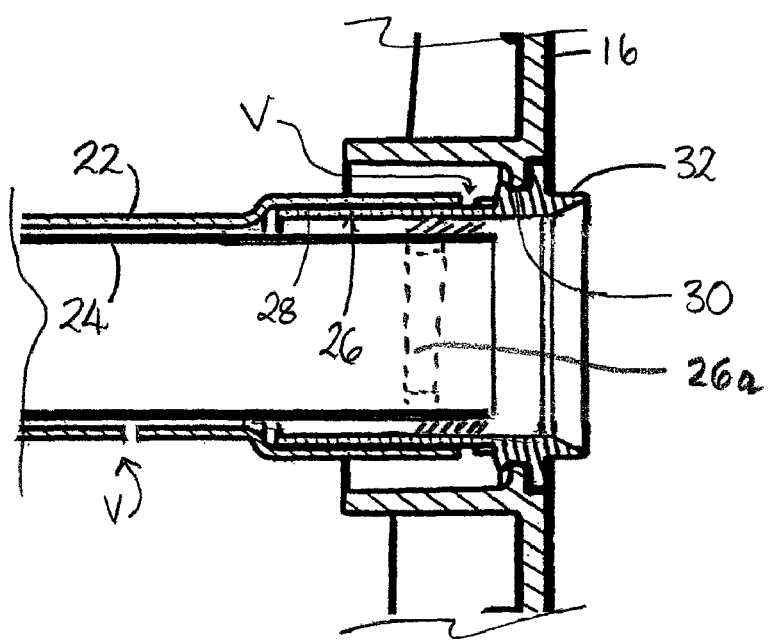
FIG. 5 is a cross-sectional view showing a further modification of the first embodiment, with a different proximal end arrangement.

In a further modified form of the first embodiment illustrated in FIG. 5, the proximal end of the second tube member 24 again passes inside the adapter tube 26, but is dimensioned not to protrude from the mouth section 32. The proximal end of the second tube member 24 is secured to the inner surface of the adapter tube 26, for example, by adhesive, welding or the introduction of an inner ring 26a to trap the film against the inside of the adapter tube.

Figure 6:
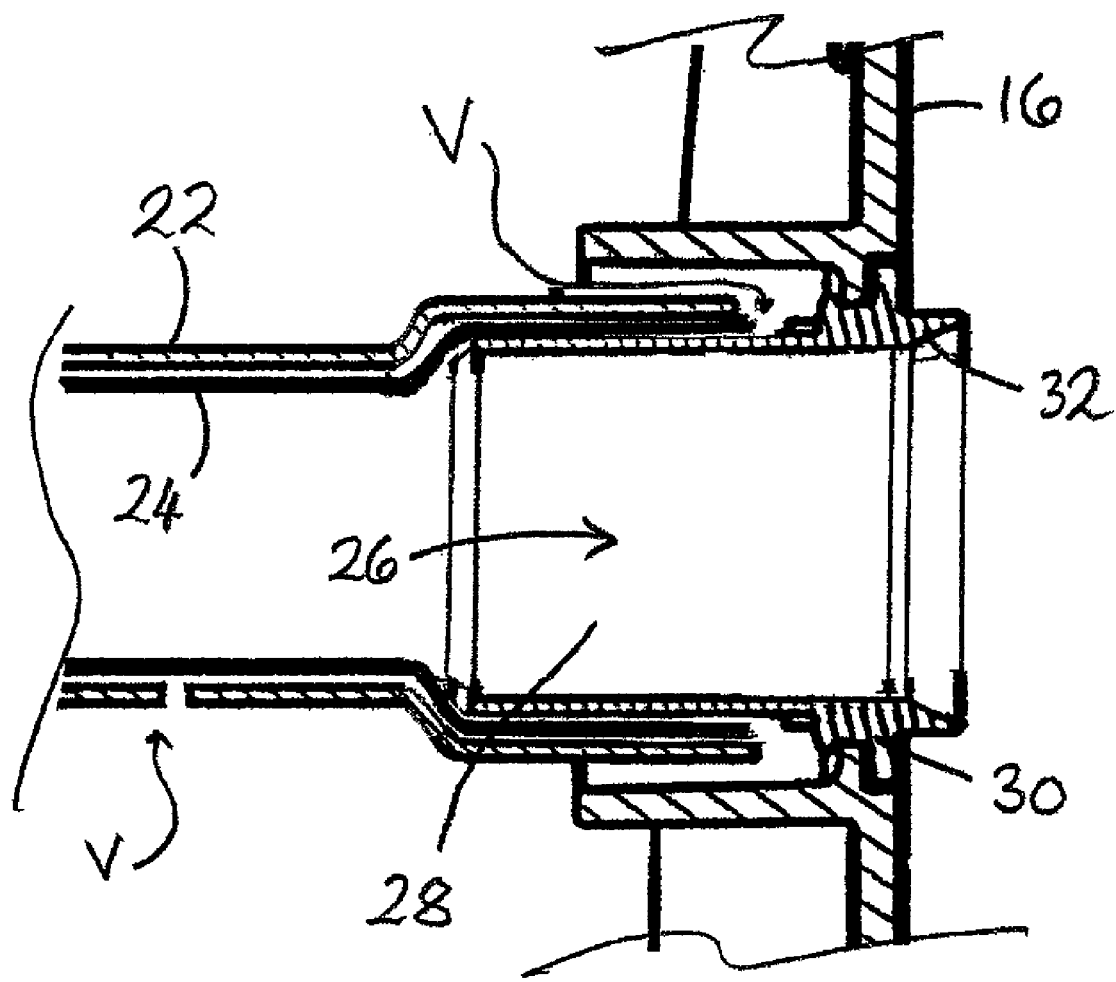
FIG. 6 is a cross-sectional view showing a further modification of the first embodiment, with a different proximal end arrangement.

In a further modified form of the first embodiment illustrated in FIG. 6, the proximal end of the second tube member 24 is not passed inside the adapter tube 26, but instead is passed over the outer surface of the tubular spigot 28 and trapped between the spigot 28 and the proximal end of the first tube member 22.

In the second embodiment illustrated in FIGS. 7 and 8, the second tube member (odor barrier sleeve) 24 is provided as an external sleeve around the first (silicone) tube member 22. A feature of an external sleeve is that the second tube member 24 does not occupy any of the internal space of the first tube member 22. In the illustrated form, the second tube member 24 closely conforms to the size of the first tube member 22. This is achieved by using a heat shrinkable material for the second tube member 22. For example, plastics film having both heat shrinkable properties and odor barrier properties based on ethylene vinyl alcohol copolymers (EVOH) or poly (vinylidene chloride) (PVDC) is available from Cryovac and Perfecseal. The odor barrier is reported to be between 4-50 $cc/m^2/day$ at 23° C., and the shrink property is reported to be at least 10%, preferably at least 30% at 100° C. The plastics film is made into a tube slightly larger in diameter than the first tube member 22. For example, if the outer diameter of the first tube member 22 is about 2.2 cm, then film for the second tube member 24 may be formed into a tube of about 2.5-3.0 cm in diameter. The second tube member 24 is then slid over the first tube member 22, and is heated to shrink down tightly around the surface of the first tube member 22. Any air or other gas trapped between the two tube members 22 and 24 may vent through one or more small vent paths. The use of shrinking down the second tube member 24 on to the first tube member 22 can avoid the need for adhesive attachment, but desired adhesive attachment may be used to reinforce the anchoring of the second tube member 24 around the first tube member 22. Optionally, the second tube member 24 can also fit loosely outside of the first tube member 22, and can be attached to each other at or near at least one end or both ends.

In addition to, or as an alternative to, the use of an odor barrier tube member distinct from the silicone tube member, another way of incorporating an odor barrier material into a silicone tube is by adding, either extrusion, coextrusion, or adhesive lamination, the odor barrier material to the silicone tube. The odor barrier layer could be as an exterior layer or a surface layer or in the middle of the silicone tube. Optionally, an adhesive layer is provided to enhance the adhesion between odor material layer and silicone. The introduction of the odor barrier layer could be during silicone tube extrusion, for example coextrusion. Or the process can take place after the silicone extrusion, for example, extrusion coating or adhesive lamination. Optionally, the odor barrier could be incorporated into a silicone sheet using adhesives and then the sheet converted into a tube form.

Figure 11:
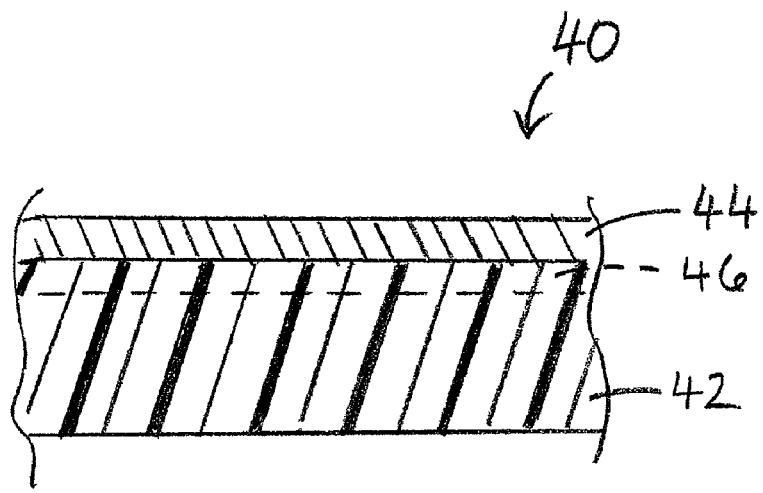
FIG. 11 is a schematic cross-sectional view showing a wall portion of the tube of the third embodiment.
Figure 12:
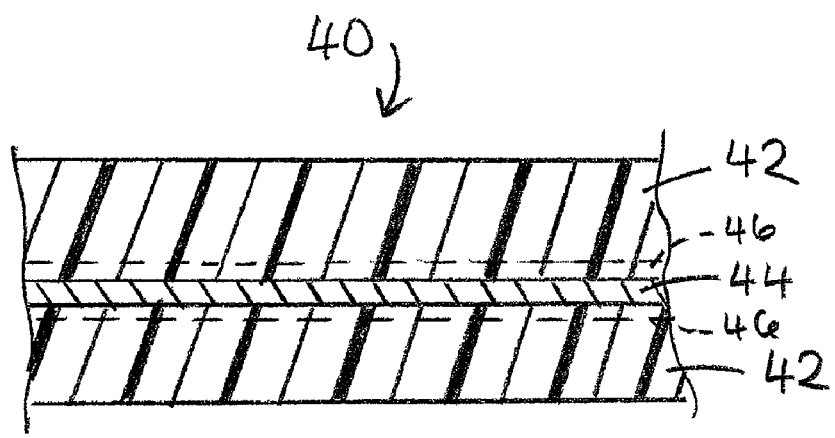
FIG. 12 is a schematic cross-sectional view showing a modified form of wall portion of the tube of the third embodiment.

FIGS. 9 and 10 illustrate a third embodiment in which the tube 12 comprises a single tube member 40. Referring to FIGS. 11 and 12, the wall of the tube member 40 is a laminate comprising at least one layer 42 of silicone based material and at least one layer 44 of odor barrier material. The odor barrier material may be any of the examples described hereinbefore. As indicated in phantom, the laminate may optionally include one or more adhesive layers 46 for bonding the odor barrier material to the silicone based material. In the example shown in FIG. 11, the odor barrier layer 44 is provided at a surface portion of the tubing 40. The surface portion may be at the radially outer surface, or the radially inner surface. In the example shown in FIG. 12, the odor barrier layer 44 is sandwiched in the middle of inner and outer layers 42 of silicone based material. The layers 42 of silicone material on either side of the odor barrier layer 44 may be of about the same thickness, one layer 42 may be thicker than the other.

It will be appreciated that the foregoing description is illustrative of preferred embodiments of the invention, and that many modifications, equivalents and improvements may be made without departing from the claim coverage of the invention.

We claim:

1. A fecal management system apparatus comprising a tube assembly for carrying malodoriforous fecal matter from the body, the tube assembly comprising:
   a. a silicone based tube having a central bore for the malodoriforous fecal matter, said tube including an inflatable balloon cuff for retaining one end of said tube within the rectum, said tube having an open end in alignment with said central bore for receiving the malodoriforous fecal matter from the rectum;
   b. a flexible, distinct, and integral tubular sleeve member within the silicone based tube, said sleeve comprising an odor barrier material of nylon and/or poly(vinylidene chloride) wherein the odor barrier material has a greater resistance to transmission of gas through the odor barrier material than that of the silicone based tube and wherein the tubular sleeve member has an oxygen transmission rate (OTR) no more than 1,000 cc/m2/day at 23° C., said tubular sleeve member being predeterminedly dimensioned to pass fecal matter therethrough;
   c. said silicone based tube and said tubular sleeve member together providing an odor barrier to obstruct leakage of odors from malodoriforous fecal matter in the bore of the silicone based tube; and
   d. an inflation conduit for in inflating the balloon cuff, wherein said inflation conduit is a conduit not integrally attached to the silicone based tube and runs inside a bore of said tubular sleeve member.

2. The fecal management apparatus according to claim 1, wherein the tubular sleeve member has a thinner wall thickness than that of the silicone based tube.

3. The fecal management apparatus according to claim 1, wherein at least a portion of the tubular sleeve member is fastened to the silicone based tube.

4. The fecal management apparatus according to claim 3, wherein said portion of the tubular sleeve member is fastened by adhesive.

5. The fecal management apparatus according to claim 4, wherein said portion is fastened by using at least one of the following: 2-part heat cure silicone adhesive, RTV silicone sealant; mechanical force; temperature; pressure.

6. The fecal management apparatus according to claim 3, wherein said portion of the tubular sleeve member is fastened at at least one end.

7. The fecal management apparatus according to claim 1, further comprising an adapter tube disposed at a first end of the silicone based tube, and wherein the tubular sleeve member is fastened to the adapter tube.

8. The fecal management apparatus according to claim 1, wherein the tubular sleeve member is made from a seamless tubular film.

9. The fecal management apparatus according to claim 1, wherein the tubular sleeve member is made of sheet material rolled into a tubular shape.

* * * * *